(12) United States Patent
Buchanan

(10) Patent No.: US 11,351,211 B1
(45) Date of Patent: Jun. 7, 2022

(54) THERAPEUTIC COMPOSITION COMPRISING BOTANICAL EXTRACTS

(71) Applicant: Kelly Allen Buchanan, Morganton, NC (US)

(72) Inventor: Kelly Allen Buchanan, Morganton, NC (US)

( * ) Notice: Subject to any disclaimer, the term of this patent is extended or adjusted under 35 U.S.C. 154(b) by 0 days.

(21) Appl. No.: 17/027,377

(22) Filed: Sep. 21, 2020

(51) Int. Cl.
| | |
|---|---|
| *A61K 36/062* | (2006.01) |
| *A61K 36/534* | (2006.01) |
| *A61K 36/906* | (2006.01) |
| *A61K 36/25* | (2006.01) |
| *A61K 36/35* | (2006.01) |
| *A61K 36/185* | (2006.01) |
| *A61K 36/28* | (2006.01) |
| *A61K 36/81* | (2006.01) |
| *A61K 36/481* | (2006.01) |
| *A61K 36/73* | (2006.01) |
| *A61K 36/23* | (2006.01) |
| *A61K 36/8945* | (2006.01) |
| *A61K 36/74* | (2006.01) |
| *A61K 36/11* | (2006.01) |
| *A61K 36/61* | (2006.01) |

(52) U.S. Cl.
CPC ............. *A61K 36/062* (2013.01); *A61K 36/11* (2013.01); *A61K 36/185* (2013.01); *A61K 36/23* (2013.01); *A61K 36/25* (2013.01); *A61K 36/28* (2013.01); *A61K 36/35* (2013.01); *A61K 36/481* (2013.01); *A61K 36/534* (2013.01); *A61K 36/61* (2013.01); *A61K 36/73* (2013.01); *A61K 36/74* (2013.01); *A61K 36/81* (2013.01); *A61K 36/8945* (2013.01); *A61K 36/906* (2013.01); *A61K 2236/333* (2013.01); *A61K 2236/37* (2013.01)

(58) Field of Classification Search
None
See application file for complete search history.

(56) References Cited

PUBLICATIONS

U.S. Appl. No. 17/174,724 filed Feb. 2021, Buchanan, K.*
Zhou, Q., National Science Review, 7:1269. (Year: 2020).*
Zhang, H E3S Web of Conferences, 308:02001. (Year: 2021).*

\* cited by examiner

*Primary Examiner* — Michael Barker

(57) ABSTRACT

The present invention relates to a composition comprising a mixed alcoholic extract of eighteen botanical ingredients formulated into capsules for the treatment of H1N1 flu, strep, pneumonia, and Covid-19.

1 Claim, No Drawings

THERAPEUTIC COMPOSITION COMPRISING BOTANICAL EXTRACTS

DETAILED DESCRIPTION OF THE INVENTION

Ingredient list for the inventive composition:
3 cups Eucalyptus (*Eucalyptus globulus*) leaves;
6 cups Spearmint (*Mentha spicata*) leaves;
4 cups Cardamon (*Elettaria cardamomum*) seed pods;
6 cups Peppermint (*Mentha piperita*) leaves;
5 cups Eleuthero (*Eleutherococcus senticosus*) root;
7 cups Valerian (*Valeriana officinalis*) whole plant;
7 cups St. John's Wort (*Hypericum perforatum*) whole plant;
5 cups whole *Usnea barbeta*;
4 cups *Echinacea purpurea* (Purple coneflower) roots, stems, and leaves;
4 cups Boneset (*Eupatorium perfoliatum*) leaves and stems;
2 cups Cayenne (*Capsicum annuum*) seed pods;
2 cups *Astragalus membranaceus* root;
2 cups Queen of the Meadow (*Eupatorium purpureum*) leaves;
3 cups Gotu Kola (*Centella asiatica*) whole plant;
7 cups Wild Yarn (*Dioscorea villosa*) root;
2 cups Yohimbe (*Pausinystalia yohimbe*) bark;
3 cups Horsetail (*Equisetum* spp.) above ground parts;
2 cups Carrot (*Daucus carota*) root.

Each of the eighteen ingredients needs to be in powder form or cut and sifted. If needed can order specialty ingredients from inventor that are personally grown and harvested and must be ground into powder form. Note the parts of the botanical ingredients are specified.

Divide the botanical ingredients into two five gallon sealable food grade buckets or sealable stainless steel kettles. Add ninety proof clear food grade alcohol until all ingredients are fully soaked and saturated. Stir with stainless steel utensils until no dry powder is left. If using electric mixer, make sure the volume of the ingredients is at a level so they are completely wet with alcohol. Once saturated, make sure to add alcohol until approximately one inch of it is on top. Check daily to check absorption rate to maintain one inch of alcohol above the ingredients to preserve and insure no molding.

Store, covered for forty-eight hours up to two weeks, depending on urgency.

Place the stored ingredients in baking pans and spread out to approximately one half inch thickness. Bake at 350 degrees for about forty-five minutes stopping periodically to scrape, turn, dice and stir until there is no moisture and ingredients are crunchy and completely dry. Do not let burn. Watch carefully and continually while in oven as the alcohol may combust or flame as it heats even if it appears dry. Attend the heating process full time.

Once cooled and completely dried, the ingredients are ground to the finest powder possible, sifted, and then placed in capsules.

The invention claimed is:

1. A composition prepared by adding ethanol to saturate the following powdered ingredients:
3 cups *Eucalyptus* leaves;
6 cups Spearmint leaves;
4 cups Cardamon seed pods;
6 cups Peppermint leaves;
5 cups Eleuthero root;
7 cups whole Valerian plant;
7 cups whole St. John's Wort plant;
5 cups whole *Usnea barbeta*;
4 cups roots, stems, and leaves of *Echinacea purpurea*;
4 cups Boneset leaves and stems;
2 cups Cayenne seed pods;
2 cups *Astragalus* root;
2 cups Queen of the Meadow leaves;
3 cups whole Gotu Kola plant;
7 cups Wild Yarn root;
2 cups Yohimbe bark;
3 cups Horsetail (above ground parts);
2 cups Carrot root,
for at least 48 hours, followed by exposing the ethanol saturated ingredients to heat to evaporate the ethanol resulting in a dry composition that is ground and formulated into capsules.

* * * * *